US00PP30739P2

(12) United States Plant Patent
Hansen

(10) Patent No.: US PP30,739 P2
(45) Date of Patent: Jul. 23, 2019

(54) ***ANEMONE* PLANT NAMED 'CURTAIN CALL PINK'**

(50) Latin Name: *Anemone hupehensis*
Varietal Denomination: Curtain Call Pink

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,161

(22) Filed: Feb. 14, 2018

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

The new and distinct cultivar of ornamental Japanese Anemone plant named *Anemone* 'Curtain Call Pink' with compact spreading habit, vertical peduncle of numerous semi-double flowers with bright rose pink petals, beginning late summer and continuing into early fall, set just above the dark green, tri-foliate leaves with irregularly serrated to bi-serrated. The new plant is useful for landscaping as a specimen, en masse, or in containers.

2 Drawing Sheets

Latin botanical classification: *Anemone hupehensis.*
Variety denomination: 'Curtain Call Pink'.

BACKGROUND OF THE INVENTION

The present invention relates to the new and distinct cultivar of Japanese Anemone, botanically known as *Anemone* 'Curtain Call Pink', and hereinafter referred to as the cultivar 'Curtain Call Pink' or the "new plant". The new plant was an intentional cross by the inventor at a wholesale perennial nursery in Zeeland, Mich., USA in the fall of 2014 between 'Pamina' (not patented) as the female or seed parent and 'Pretty Lady Emily' U.S. Plant Pat. No. 22,303 as the male or pollen parent. The seed were harvested and the new plant was assigned the breeder code 14-18-24 during the evaluation process at the same nursery. *Anemone* 'Curtain Call Pink' has been asexually propagated through root cuttings first in October of 2016 at the same nursery in Zeeland, Mich. and subsequently also by sterile plant tissue culture. Plants of 'Curtain Call Pink' have been found to be stable and identical to the original selection in multiple generations of asexual propagation.

No plants of *Anemone* 'Curtain Call Pink' have been sold, in this country or anywhere in the world, prior to the filing of this application, nor has any disclosure of the new plant been made prior to the filing of this application except that which was disclosed within one year of the filing of this application and was either derived directly or indirectly from the inventor.

'Curtain Call Pink' has not been observed under all possible environments. The phenotype may vary slightly with different environmental conditions, such as temperature, light, fertility, moisture and maturity levels, but without any change in the genotype.

BRIEF SUMMARY OF THE PLANT

'Curtain Call Pink' is unique from all other Japanese Anemone known to the inventor. The new plant compares most closely with its parent 'Pretty Lady Emily'. Compared to 'Pretty Lady Emily' the new plant is slightly taller and more flowers per plant. In comparison to 'Pamina (not patented) the new plant has slightly different colored flowers that are closer to purple in hue, more uniformly semi-double flower, has shorter habit and better branching. 'Pretty Lady Diana' U.S. Plant Pat. No. 22,332 has single flowers with typically five petals per flower of deep rose pink and light pink. 'Pretty Lady Susan' U.S. Plant Pat. No. 22,331 has single flowers with typically five petals per flower of deep pink. 'Pretty Lady Julia' U.S. Plant Pat. No. 23,131 has semi-double flowers with about 28 petals per flower of pink and light pink color. The flowers of the new plant have petals that are lighter and more uniform in color than all of the above cultivars.

The new plant, *Anemone* 'Curtain Call Pink', is distinct from all other Japanese Anemone known to the inventor through the following combined characteristics:

1. Semi-double flowers of bright rose pink on branched panicle.
2. Flowering beginning late summer flowering and continuing into early fall.
3. Compact spreading habit with dark green foliage.

BRIEF DESCRIPTION OF THE DRAWINGS

The photographs of the new plant demonstrate the unique traits and the overall appearance of *Anemone* 'Curtain Call Pink'. The colors are as accurate as reasonably possible with color reproductions. Variation in ambient light spectrum, source and direction may cause the appearance of minor variation in color. The plant used in the photographs was a two-year-old plant grown in a full-sun nursery trial garden in Zeeland, Mich. with supplemental water and fertilizer when needed. No pinching or plant growth regulators have been, used.

DETAILED BOTANICAL DESCRIPTION

Figure 1:
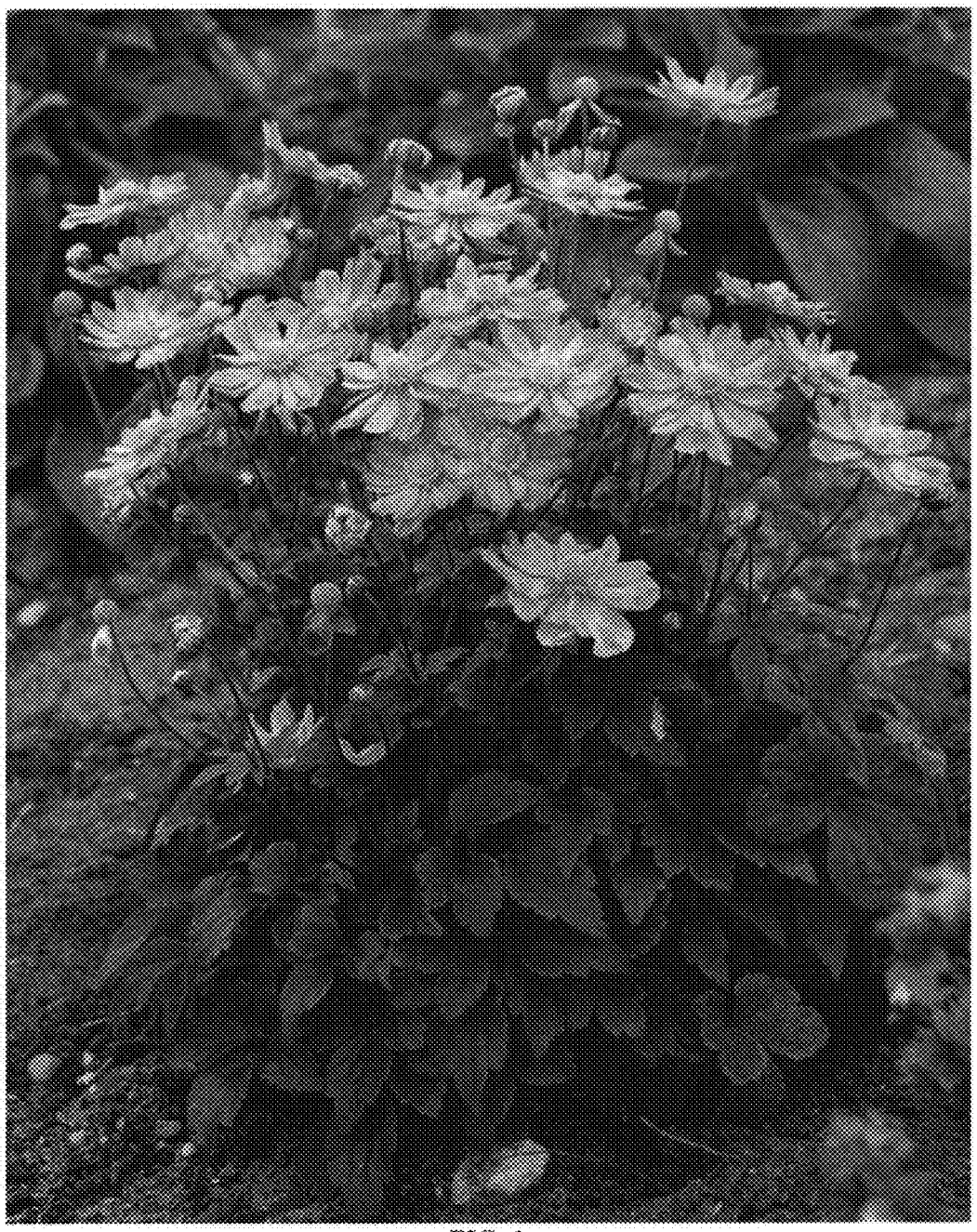
FIG. 1 shows the new plant in mid-season flowering habit.
Figure 2:
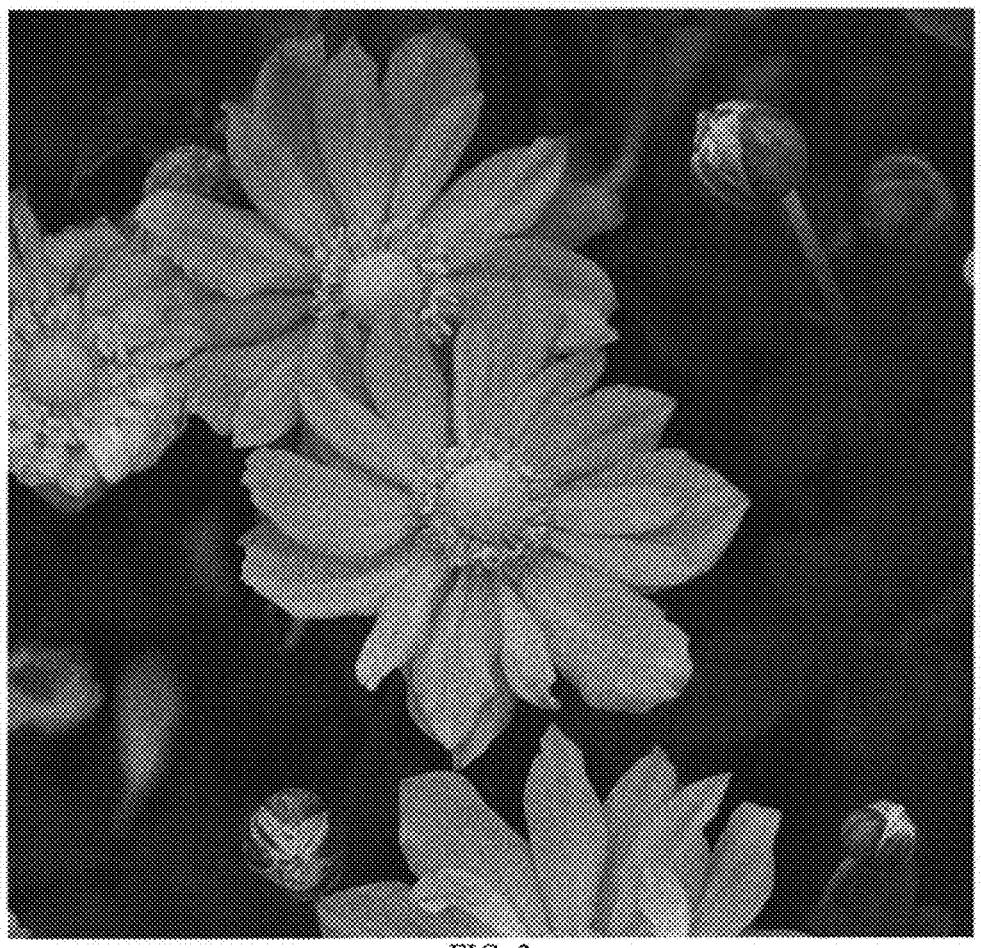
FIG. 2 shows a close-up of the flower scape.

The following descriptions and color references are based on the 2015 edition of The Royal Horticultural Society Colour Chart except where common dictionary terms are used. *Anemone* 'Curtain Call Pink' has not been observed under all possible environments. The phenotype may vary slightly with different growing environments such as temperature, light, fertility, soil pH, moisture and plant maturity levels, but without any change in the genotype. The following observations and size descriptions are based on two-year-old plants growing in full-sun trial garden in Zeeland, Mich. Plants were given supplemental water and fertilizer but no plant growth regulators were used.

*Parentage.*—Female or seed parent is 'Pamina'; male or pollen parent is 'Pretty Lady Emily'.

*Plant habit.*—Hardy herbaceous perennial; small mounded foliage with flowers arranged on branched raceme just above foliage; foliage height to about 25.0 cm tall and flower height to about 40.0 cm tall; plant width about 45.0 cm at widest point at about 20 cm above soil level.

*Growth rate.*—Moderately vigorous, finishing in a 65 mm plug from a rooted Stage 3 tissue culture explants in about 8 weeks and finishing in a 3.8 liter container from a 65 mm plug in about 8 weeks.

*Root.*—Fine, fibrous; less than 0.5 mm diameter; heavily branched; color nearest RHS 165C.

*Foliage.*—Tri-foliate, cleft to petiole; center lobe ovate, with side lobes ovate to irregularly dissected; apex typically acute; base rounded, frequently imbricate; margin irregularly serrate to bi-serrate; adaxial and abaxial surfaces glabrous; mostly basal; leaf attitude slightly drooping; cauline leaves decreasing in size and with more acute apex.

*Leaf size.*—Average about 6.5 cm long and 5.5 cm across, center lobe to about 4.0 cm long and 2.5 cm across; side lobes average about 3.2 cm long and 2.2 cm across.

*Leaf blade color.*—Emerging adaxial nearest RHS 143A, abaxial nearest RHS 143B; mature adaxial nearest blend nearest RHS 139A, abaxial blend between RHS 147C and RHS 137C.

*Veins.*—Palmate; puberulent and slightly impressed on adaxial surface and slightly ridged and puberulent on abaxial surface.

*Vein color.*—Same as surrounding leaf tissue.

*Petiole.*—Terete; puberulent, dull; about 2.5 cm long and about 2.5 mm diameter at base; cauline leaves sessile.

*Petiole color.*—Nearest RHS 139A.

*Flower attitude.*—Upright.

*Inflorescence.*—Terminal corymb; with gynoecium surrounded by numerous androecium; average size flowering panicle about 6.5 cm across and about 2.0 cm tall; about 2 to 4 flowers per branched peduncle; with about 70 flowers per plant; flower timing in Michigan begins late summer and continues for about four weeks on the plant.

*Buds about two days prior to anthesis and after sepals split.*—Globose with rounded apex and rounded base; about 1.5 cm diameter and about 1.5 cm tall.

*Bud color.*—Sepals nearest RHS N186D with petals showing between sepals nearest RHS 202D.

*Petals.*—Spatulate; with acute apex, attenuate base; entire margin; glabrous; irregularly sized, to 2.7 cm long and 1.4 cm wide near apex, average about 2.5 cm long and 10.0 mm wide near apex; about 24 petals per flower.

*Petal color.*—Adaxial blend between RHS 75C and RHS 73C; abaxial between RHS 75C and RHS 73D.

*Flower fragrance.*—None detected.

*Flower persistence.*—Self-cleaning.

*Gynoecium.*—Numerous; in domed cap; average 10.0 mm across and 7.5 mm tall.

*Androecium.*—Numerous; about 100; Filaments: fine; terete; about 3.5 mm long and less than 0.2 mm diameter; color nearest RHS 145C. Stamens: ellipsoidal; basifixed; longitudinal; rounded apex and base; about 2.0 mm long and 1.0 mm across; color nearest RHS 15A; Pollen: abundant; color nearest RHS N25B.

*Calyx.*—Ovate; strongly cupped; acute apex and base fused; margin entire; puberulent abaxial, glabrous adaxial; typically about 5 per flower; color nearest RHS 148B with strong tinting of RHS 187A.

*Peduncle.*—About 25 per plant; terete; pubescent; attitude vertical; to about 40 cm long and 3.0 mm diameter at base.

*Peduncle color.*—Nearest RHS NN137A.

*Fruit and seed have not yet been observed.*

*Hardiness, pest and disease resistance.*—The new plant grows best with ample moisture, adequate drainage and shade from hot sun. Hardiness at least from USDA zone 5 zone 9. Disease and pest resistance beyond what is typical of that of other Japanese Anemone has not been observed.

I claim:

1. A new and distinct cultivar of ornamental Japanese Anemone plant named *Anemone* 'Curtain Call Pink', as herein described and illustrated.

* * * * *